United States Patent
Nyqvist et al.

(10) Patent No.: US 6,858,645 B2
(45) Date of Patent: Feb. 22, 2005

(54) TARTRATE SALTS OF (R) -3-N,N-DICYCLOBUTYLAMINO-8-FLUORO-3,4-DIHYDRO-2H-1- BENZOPYRAN-5-CARBOXAMIDE

(75) Inventors: Hakan Nyqvist, Södertälje (SE); Daniel D Sohn, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/077,718

(22) PCT Filed: May 15, 1998

(86) PCT No.: PCT/SE98/00907

§ 371 (c)(1),
(2), (4) Date: Jun. 8, 1998

(87) PCT Pub. No.: WO98/54166

PCT Pub. Date: Dec. 3, 1998

(65) Prior Publication Data

US 2003/0109576 A1 Jun. 12, 2003

(30) Foreign Application Priority Data

May 30, 1997 (SE) .............................................. 9702066

(51) Int. Cl.⁷ ..................... A61K 31/353; C07D 311/58

(52) U.S. Cl. ......................... 514/456; 514/457; 549/404
(58) Field of Search .................. 514/456, 457; 549/404

(56) References Cited

U.S. PATENT DOCUMENTS

| 5,616,610 A | 4/1997 | Evenden et al. |
| 5,990,114 A | 11/1999 | Leonardi et al. |

FOREIGN PATENT DOCUMENTS

| WO | 9511891 | 5/1995 |
| WO | 9731637 | 9/1997 |

*Primary Examiner*—Taofiq Solola
(74) *Attorney, Agent, or Firm*—White & Case LLP

(57) ABSTRACT

A new salt (R)-3-N,N-dicyclobutylamino-8-fluoro-3,4-dihydro-2H-1-benzopyran-5-carboxamide hydrogen tartrate, particularly the (2R,3R)-tartrate thereof, most particularly the (R)-3-N,N-dicyclobutylamino-8-fluoro-3,4-dihydro-2H-1-benzopyran-5-carboxamide hydrogen (2R, 3R)-tartrate monohydrate, processes for the manufacture of said tartrate salt, the use of the salt in medicine, the use of the tartrate salt in the manufacture of pharmaceutical formulations, and a method for the treatment of CNS disorders by administration of the tartrate salt to a host in need of such treatment.

8 Claims, 2 Drawing Sheets

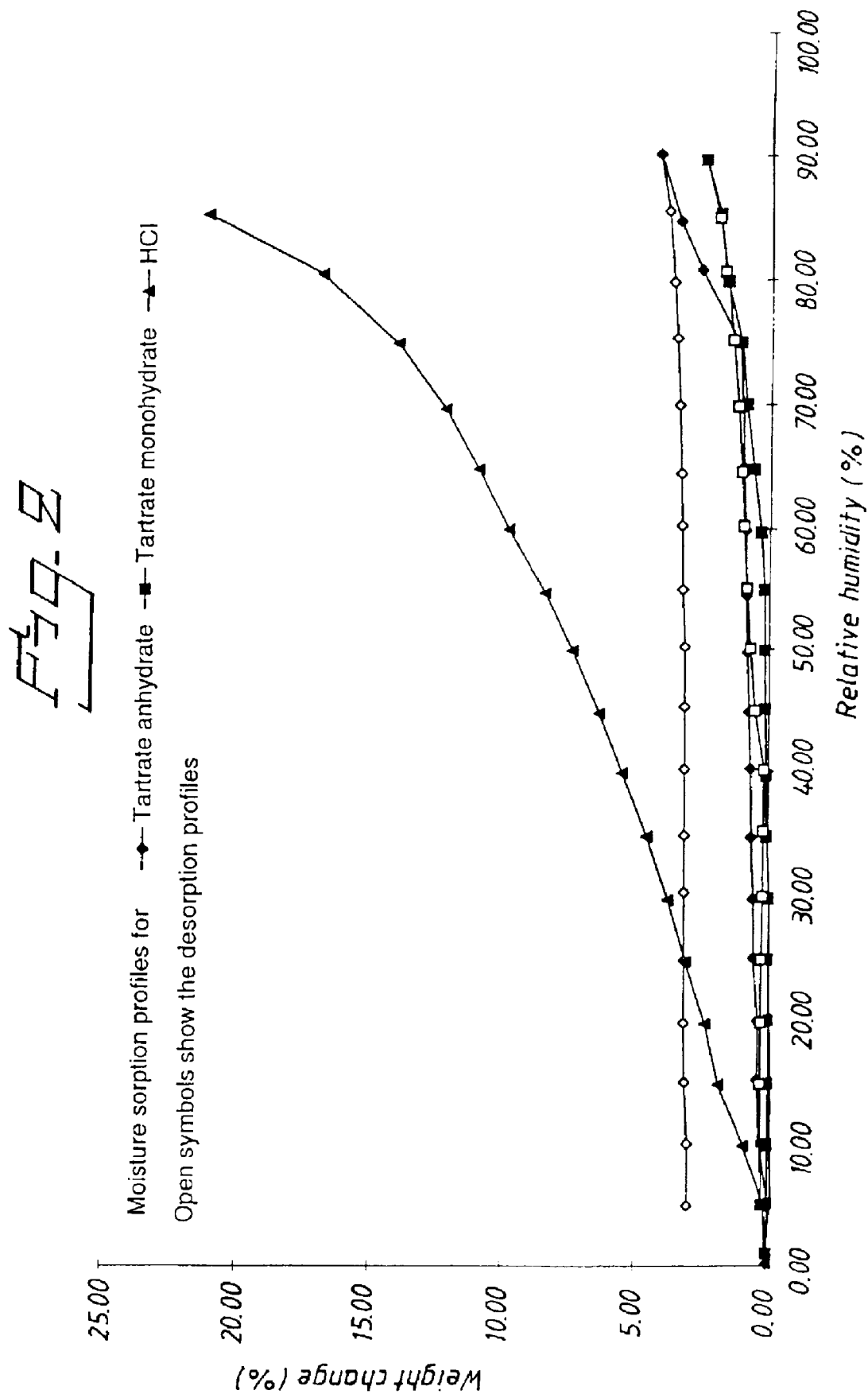

Figure 1:
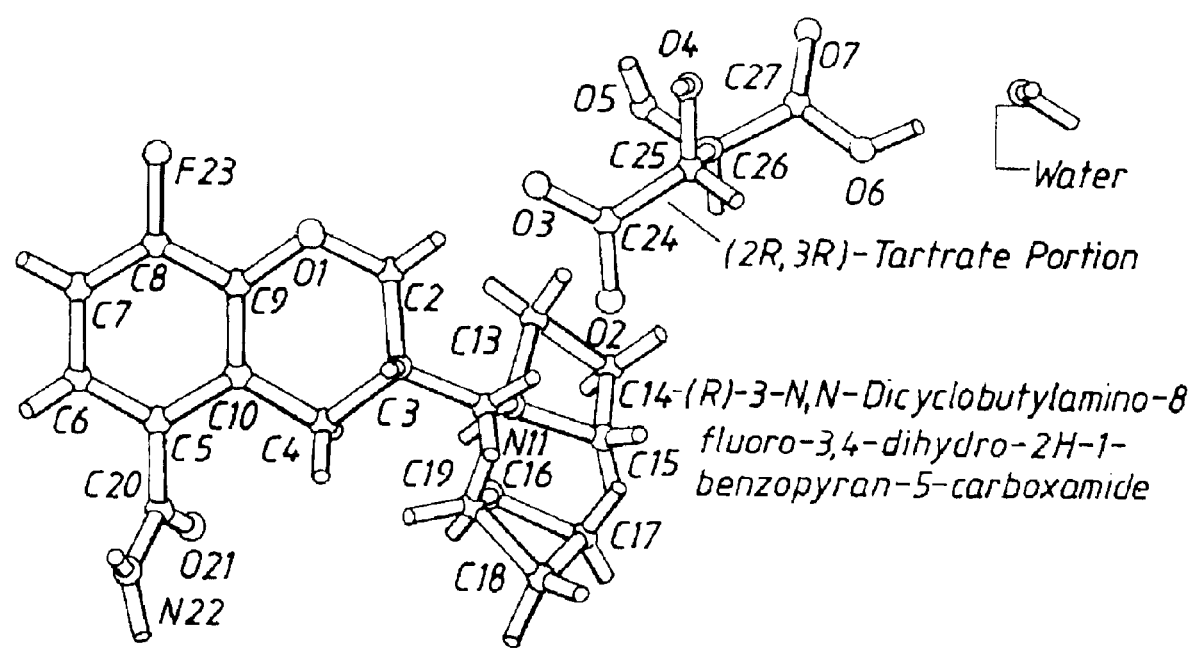

TARTRATE SALTS OF (R) -3-N,N-DICYCLOBUTYLAMINO-8-FLUORO-3,4-DIHYDRO-2H-1- BENZOPYRAN-5-CARBOXAMIDE

This is a 371 of PCT/SE98/00907 filed May 15, 1998 which claims the priority of Application No. 9702066-3 filed in Sweden on May 30, 1997.

FIELD OF THE INVENTION

The present invention relates to a new salt, namely (R)-3-N,N-dicyclobutylamino-8-fluoro-3,4-dihydro-2H-1-benzopyran-5-carboxamide hydrogen tartrate, particularly the (2R,3R) form of the tartrate and most particularly the monohydrate thereof. The invention also relates to processes for the manufacturing of the salt, the use of the salt in the manufacture of pharmaceutical formulations, to the use of the salt in medicine and methods of treatment employing the salt particularly in its monohydrate form.

BACKGROUND OF THE INVENTION

The compound (R)-5-carbamoyl-3-N,N-dicyclobutylamino-8-fluoro-3,4-dihydro-2H-1-benzopyran, which also may be named (R)-3-N,N-dicyclobutylamino-8-fluoro-3,4-dihydro-2H-1-benzopyran-5-carboxamide and pharmaceutically acceptable salts thereof are described in WO 95/11891.

The disclosed hydrochloride salt of (R)-3-N,N-dicyclobutylamino-8-fluoro-3,4-dihydro-2H-1-benzopyran-5-carboxamide is hygroscopic and thus physically unstable during manufacturing as well as during storage.

DISCLOSURE OF THE INVENTION

It has now surprisingly been found that the salt (R)-3-N,N-dicyclobutylamino-8-fluoro-3,4-dihydro-2H-1-benzopyran-5-carboxamide hydrogen tartrate, particularly the (2R,3R) form of the tartrate, in the anhydrous form or as the hemihydrate or monohydrate is physically more stable during storage than the hydrochloride salt of said compound, since the tartrate forms of the compound are not disposed to absorb water to the same degree as the hydrochloride salt of the same compound. This property of absorbing water is also a problem during storage and during manufacture of, e.g., solid pharmaceutical dosage forms such as tablets and hard gelatine capsules.

The good solubility and dissolution properties of the anhydrous tartrate salt are even more pronounced for the monohydrate of the tartrate salt, particularly the (2R,3R)-tartrate monhydrate. The water is firmly bound in the crystal lattice and is not released even upon heating up to 70° C. This is well above the commonly used process temperatures, e.g., during the granulation process, in the production of tablets and hard gelatine capsules.

The good solubility and dissolution properties of the tartrate salt from, e.g., the oral drug delivery point of view, together with the low degree of hygroscopicity under normal humidity conditions makes the monohydrate form the most suitable form of the tartrate salt, and particularly the (2R, 3R)-tartrate monohydrate from a quality assurance standpoint.

Thus, the monohydrate of (R)-3-N,N-dicyclobutylamino-8-fluoro-3,4-dihydro-2H-1-benzopyran-5-carboxamide hydrogen (2R,3R)-tartrate, has surprisingly been shown to be physically stable under normal humidity conditions, to be suitable for long term storage and to be easier to work with in the production of different solid pharmaceutical dosage forms.

Accordingly, the present invention relates to the salt (R)-3-N,N-dicyclobutylamino-8-fluoro-3,4-dihydro-2H-1-benzopyran-5-carboxamide hydrogen tartrate, particularly to the salt (R)-3-N,N-dicyclobutylamino-8-fluoro-3,4-dihydro-2H-1-benzopyran-5-carboxamide hydrogen (2R, 3R)-tartrate and more particularly to the salt (R)-3-N,N-dicyclobutylamino-8-fluoro-3,4-dihydro-2H-1-benzopyran-5-carboxamide hydrogen (2R,3R)-tartrate monohydrate.

The present invention includes (R)-3-N,N-dicyclobutylamino-8-fluoro-3,4-dihydro-2H-1-benzopyran-5-carboxamide hydrogen tartrate, in the form of (2R,3R)-tartrate, (2S,3S)-tartrate and (2R,3S)-tartrate.

The salts of the invention may be used as selective 5-$HT_{1A}$ receptor antagonists in the treatment of CNS disorders and related medical disturbances. Examples of such disorders are depression, anxiety, obsessive-compulsive disorder (OCD), anorexia, bulimia, senile dementia, migraine, stroke, Alzheimer's disease, cognitive disorders, schizophrenia, especially cognitive dysfunction in schizophrenia, sleep disorders, urinary incontinence, premenstrual syndrome, hypertension and pain. Examples of such medical disturbances are thermoregulatory disturbances, sexual disturbances, disturbances in the cardiovascular system and disturbances in the gastrointestinal system.

The novel salt (R)-3-N,N-dicyclobutylamino-8-fluoro-3, 4-dihydro-2H-1-benzopyran-5-carboxamide hydrogen tartrate, particularly the (2R,3R) form of the tartrate and most particularly the monohydrate of said tartrate salt existing preferably in substantially crystalline form may be formulated into various dosage forms for oral, parenteral, rectal and other modes of administration.

Examples of formulations are tablets, pellets, granules, capsules (e.g. hard gelatine capsules), aqueous solutions and suspensions.

Usually the active ingredient will constitute from 0.0001 to 99% by weight of the formulation, more preferably from 0.001 to 30% by weight of the formulation.

To produce pharmaceutical formulations containing the active ingredient of the invention in the form of dosage units for oral applications, one may mix the active ingredient with a solid excipient, e.g. lactose, saccharose, sorbitol, mannitol, starches such as potato starch, corn starch or amylopectin, a cellulose derivative, a binder such as gelatine or polyvinylpyrrolidone, and a lubricant such as magnesium stearate, calcium stearate, sodium stearylfumarate, polyethylene glycol, waxes, paraffin, and the like, and then compres the components into tablets. The active ingredient may be granulated together with excipients using an aqueous or organic solution of binders, and then dried and screened prior to tablet compression.

If coated tablets are required, the cores, prepared as described above, may be coated with a concentrated sugar solution which may contain, e.g., gum arabic, gelatine, talcum, titanium dioxide, and the like. Alternatively, the tablet can be coated with a polymer known to a person skilled in the art, that is dissolved in a readily volatile organic solvent or mixture of organic solvents. Dyestuffs may be added to these coatings in order to readily distinguish between tablets containing different amounts of active ingredient.

For the preparation of hard gelatine capsules, the active ingredient may be processed in the form of granules, and may be admixed with the excipients mentioned above for tablets.

For the preparation of soft gelatine capsules, the active ingredient may be admixed with e.g. a vegetable oil or polyethylene glycol.

Suppositories for rectal administration may be prepared by dissolving or suspending the active ingredient in a molten suppository base such as Witepsol® followed by casting and cooling.

Gelatine rectal capsules may comprise the active ingredient in admixture with vegetable oil or paraffin oil and may contain some of the polymers and/or dyestuffs mentioned above.

Aqueous solutions for parenteral or oral administration are produced by dissolving the active compound of the invention in water, adjusting the pH and ionic strength with common buffering agents such as citric acid, phosphoric acid or other similar acids or their commonly used salts; sodium carbonate, hydrogen carbonate or other similar salts; or hydrochloric acid or sodium hydroxide. In the case of parenteral solutions the sterility is ensured by final heat sterilization or, e.g., sterile filtration. Lyophilization, resulting in a reconstitutable solid product, may also be used.

Suitable daily doses of the salt of the invention in therapeutical treatment of humans are about 0.001–100 mg/kg body weight.

The specific processes for manufacturing (R)-3-N,N-dicyclobutylamino-8-fluoro-3,4-dihydro-2H-1-benzopyran-5-carboxamide hydrogen (2R,3R)-tartrate, (2S,3S)-tartrate or (2R,3S)-tartrate, respectively, more specifically the monohydrate thereof, are a further aspect of the invention.

The process for manufacturing the new salt form (R)-3-N,N-dicyclobutylamino-8-fluoro-3,4-dihydro-2H-1-benzopyran-5-carboxamide hydrogen (2R,3R)-tartrate, more specifically the monohydrate thereof, comprises the following consecutive steps:

i) dissolving (R)-3-N,N-dicyclobutylamino-8-fluoro-3,4-dihydro-2H-1-benzopyran-5-carboxamide in an appropriate organic solvent, optionally by heating, ii) adding (2R,3R)-tartaric acid dissolved in an appropriate aqueous organic or non-aqueous organic solvent, iii) allowing the obtained solution to stand cold in order to crystallize, iv) optionally, recrystallizing from an aqueous organic solvent, if a non-aqueous organic solvent is used in step ii), to obtain the tartrate monohydrate salt.

The corresponding (2S,3S)-tartrate and (2R,3S)-tartrate compound are manufactured by using (2S,3S)-tartaric acid and (2R,3S)-tartaric acid, respectively in step ii) above.

A more detailed description of the process of manufacturing is presented in Examples 1 and 2.

Starting from the anhydrous form or a mixture of the anhydrous form and the hemihydrate of (R)-3-N,N-dicyclobutylamino-8-fluoro-3,4-dihydro-2H-1-benzopyran-5-carboxamide hydrogen (2R,3R), (2S,3S) or (2R,3S)-tartrate, obtained by any suitable process, recrystallization of the tartrate from an appropriate aqueous organic solvent will give the monohydrate of the invention.

Appropriate solvents for dissolving (R)-3-N,N-dicyclobutylamino-8-fluoro-3,4-dihydro-2H-1-benzopyran-5-carboxamide may be organic solvents such as tetrahydrofuran, diethyl ether, acetone, ethanol, methanol and other alcohols.

Appropriate aqueous organic solvents used in the crystallization or recrystallization may be alcohols, nitriles, esters, or ketones e.g. methanol, ethanol, isopropanol, acetonitrile, or acetone, preferably acetone.

EXAMPLE 1

(R)-3-N,N-Dicyclobutylamino-8-fluoro-3,4-dihydro-2H-1-benzopyran-5-carboxamide Hydrogen (2R, 3R)-Tartrate (R)-3-N,N-Dicyclobutylamino-8-fluoro-3,4-dihydro-2H-1-benzopyran-5-carboxamide (100 mg, 0.31 mmol) was dissolved in tetrahydrofuran (1 mL) by heating and the solution was diluted with diethyl ether (25 mL). To this solution was added a solution of (2R, 3R)-tartaric acid made by dissolving 55 mg (0.35 mmol) of (2R,3R)-tartaric acid in tetrahydrofuran (1 mL) and diluting with diethyl ether (25 mL). The milky solution obtained was filtered and allowed to stand in the refrigerator overnight. The solid was filtered and dried in a vacuum oven to give the title compound in 142 mg white crystals (98% yield). Mp 174–180° C. (DSC). Anal. Calcd. for $C_{22}H_{23}FN_2O_8$: C, 56.4; H, 6.2; N, 6.0. Found: C, 56.2; H, 5.9; N, 5.6.

EXAMPLE 2

(R)-3-N,N-dicyclobutylamino-8-fluoro-3,4-dihydro-2H-1-benzopyran-5-carboxamide Hydrogen (2R, 3R)-Tartrate Monohydrate (R)-3-N,N-Dicyclobutylamino-8-fluoro-3,4-dihydro-2H-1-benzopyran-5-carboxamide (2.0 g, 6.3 mmol) was dissolved in tetrahydrofuran (5 mL) by heating and the solution was diluted with diethyl ether (400 mL). To this solution was added a solution of (2R, 3R)-tartaric acid made by dissolving 1.1 g (6.9 mmol) of (2R, 3R)-tartaric acid in tetrahydrofuran (15 mL) and diluting with diethyl ether (300 mL). The clear solution obtained was allowed to stand in the refrigerator over the weekend. The crystalline solid obtained was filtered and recrystallized from 1.5% aqueous acetone (400 mL) to give of the title compound 2.6 g sparkly crystals (85% yield). Mp. 174–180° C. (DSC). Anal. Calcd. for $C_{22}H_{25}FN_2O_9$: C, 54.3; H, 6.4; N, 5.8. Found: C, 54.4; H, 6.3; N, 5.6.

Analytical Test Method Used on the Products Obtained in Examples 1 and 2

The melting point (Mp) was measured by using differential scanning calorimetry (DSC).

Establishment of Water Content a) Thermogravimetric Assay

Thermogravimetric measurements performed showed that the anhydrous form of (R)-3-N,N-dicyclobutylamino-8-fluoro-3,4-dihydro-2H-1-benzopyran-5-carboxamide hydrogen (2R,3R)-tartrate obtained in Example 1 had an initial weight loss of 0.997% w/w. The initial weight loss of 4.104% w/w for the monohydrate of (R)-3-N,N-dicyclobutylamino-8-fluoro-3,4-dihydro-2H-1-benzopyran-5-carboxamide hydrogen (2R,3R)-tartrate obtained in Example 2 compared favourably with the theoretical water content of a monohydrate.

b) X-Ray Diffraction

X-ray intensity data were collected on a single-crystal MACH3/CAD4 diffractometer (Enraf-Nonius, 1994) equipped with graphite monochromatic CuK($\alpha$) radiation and a proportional scintillation counter. The structure was solved by direct methods, SIR92 (Altomare, Cascarano, Giacovazzo & Guagliardi, 1992) and refined with full-matrix least-square methods, LSFM (Hansen & Coppens, 1974), within the MolEN software package (Straver & Schierbeck, 1994). All non-hydrogen atoms were refined anisotropically, whereas hydrogen atoms not involved in short intermolecular contacts were fixed from a late difference Fourier and supplied with isotropic displacement parameters, $U_{iso}$=0.06 Å$^2$. Hydrogen atom positions involved in H-bonding were refined freely and assisted with a fixed isotropic temperature factor, $U_{iso}$=0.06 Å$^2$, except for the crystal water hydrogens for which the factor used was $U_{iso}$=0.07 Å$^2$.

FIG. 1 shows the three-dimensional structure and absolute configuration of (R)-3-N,N-dicyclobutylarnino-8-fluoro-3, 4-dihydro-2H-1-benzopyran-5-carboxamide in relationship to the (2R,3R)-tartrate portion and the water molecule.

Determination of Stability

Moisture sorption of the monohydrate of (R)-3-N,N-dicyclobutylamino-8-fluoro-3,4-dihydro-2H-1-benzopyran-5-carboxamide hydrogen (2R,3R)-tartrate compared to that of the anhydrous form of (R)-3-N,N-dicyclobutylamino-8-fluoro-3,4-dihydro-2H-1-benzopyran-5-carboxamide hydrogen (2R,3R)-tartrate, as well as to that of the HCl-salt has been set as a measure of the relative physical stabilities of the respective products.

The moisture sorption analysis, absorption and desorption, respective was performed using a VTI microbalance, Model MB300W (VTI Corporation, USA) linked to an IBM PC. The relative humidity (RH) within the balance was monitored using a dew point analyser. Approximately 10 mg of substance was dried to constant weight at 60° C. and then exposed stepwise to RHs of from 5 to 90% at 25° C., the step interval being 5%. The desorption profile was also obtained.

FIG. 2 shows the moisture sorption curve of the HCl salt of (R)-3-N,N-dicyclobutylamino-8-fluoro-3,4-dihydro-2H-1-benzopyran-5-carboxamide. As seen from the figure, the HCl salt takes up a considerable amount of moisture at high relative humidities. At 85% relative humidity the HCl salt has taken up approximately 20% w/w and exhibits deliquescence.

FIG. 2 also shows the moisture sorption curve of the anhydrous form (anhydrate) of (R)-3-N,N-dicyclobutylamino-8-fluoro-3,4-dihydro-2H-1-benzopyran-5-carboxamide hydrogen (2R,3R)-tartrate. As seen from the figure, the anhydrous form (anhydrate) absorbs moisture readily. At a RH of 90%, about 4.2% (w/w) moisture was absorbed. The desorption profile (the upper part of the curve) indicates that the moisture taken up is firmly bound and that the sample has formed a monohydrate.

FIG. 2 shows the moisture sorption curve of the monohydrate of (R)-3-N,N-dicyclobutylamino-8-fluoro-3,4-dihydro-2H-1-benzopyran-5-carboxamide hydrogen (2R,3R)-tartrate. As seen from the figure the monohydrate absorbs only 2.5% (w/w) at 90% RH. Significant uptake of moisture was only recorded at RH of approximately 60% or above. The desorption profile shows that the moisture uptake is reversible.

What is claimed is:

1. The salt (R)-3-N,N-dicyclobutylamino-8-3,4-dihydro-2H-1-benzopyran-5-carboxamide hydrogen (2R3R)-tartrate monohydrate.

2. The salt according to claim 1 in crystalline form.

3. A pharmaceutical formulation comprising, as active ingredient, the salt according to claim 1 or 2 in association with a suitable diluent, excipient or an inert carrier.

4. A method for the treatment of a condition selected from the grouping consisting of depression and anxiety comprising administration, to a host in need of such treatment, an effective amount of the salt according to claim 1 or 2.

5. The method according to claim 4, wherein the condition is depression.

6. The method according to claim 4, wherein the condition is anxiety.

7. The pharmaceutical formulation according to claim 3, wherein the pharmaceutical formulation is an oral dosage form.

8. The pharmaceutical formulation according to claim 3 further comprising a lubricant.

* * * * *

UNITED STATES PATENT AND TRADEMARK OFFICE
CERTIFICATE OF CORRECTION

PATENT NO. : 6,858,645 B2
DATED : February 22, 2005
INVENTOR(S) : Nyqvist et al.

It is certified that error appears in the above-identified patent and that said Letters Patent is hereby corrected as shown below:

Column 6,
Line 13, "8-3,4-dihydro" should read -- 8-fluoro-3,4-dihydro --.
Line 14, "(2R3R)" should read -- (2R,3R) --.

Signed and Sealed this

Tenth Day of May, 2005

JON W. DUDAS
*Director of the United States Patent and Trademark Office*